(12) United States Patent
Buettelmann et al.

(10) Patent No.: US 9,708,340 B2
(45) Date of Patent: Jul. 18, 2017

(54) UREA DERIVATIVES AND THEIR USE AS FATTY-ACID BINDING PROTEIN (FABP) INHIBITORS

(71) Applicant: Hoffmann-La Roche Inc., Little Falls, NJ (US)

(72) Inventors: Bernd Buettelmann, Schopfheim (DE); Simona M. Ceccarelli, Basel (CH); Aurelia Conte, Basel (CH); Holger Kuehne, Loerrach (DE); Bernd Kuhn, Reinach (CH); Werner Neidhart, Hagenthal-le-Bas (FR); Ulrike Obst Sander, Reinach (CH); Hans Richter, Grenzach-Wyhlen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/856,325

(22) Filed: Sep. 16, 2015

(65) Prior Publication Data
US 2016/0185795 A1    Jun. 30, 2016

Related U.S. Application Data

(63) Continuation of application No. PCT/EP2014/055222, filed on Mar. 17, 2014.

(30) Foreign Application Priority Data

Mar. 20, 2013  (EP) .................................. 13160084

(51) Int. Cl.
| | | |
|---|---|---|
| C07D 211/00 | (2006.01) | |
| C07D 295/00 | (2006.01) | |
| A61K 31/445 | (2006.01) | |
| C07D 495/04 | (2006.01) | |
| C07D 213/79 | (2006.01) | |
| C07D 401/12 | (2006.01) | |
| C07D 409/12 | (2006.01) | |
| C07D 205/04 | (2006.01) | |
| C07D 207/16 | (2006.01) | |
| C07D 277/06 | (2006.01) | |
| C07D 209/52 | (2006.01) | |
| C07D 211/60 | (2006.01) | |

(52) U.S. Cl.
CPC ......... *C07D 495/04* (2013.01); *C07D 205/04* (2013.01); *C07D 207/16* (2013.01); *C07D 209/52* (2013.01); *C07D 211/60* (2013.01); *C07D 213/79* (2013.01); *C07D 277/06* (2013.01); *C07D 401/12* (2013.01); *C07D 409/12* (2013.01)

(58) Field of Classification Search
None
See application file for complete search history.

(56) References Cited

U.S. PATENT DOCUMENTS

| | | | | |
|---|---|---|---|---|
| 3,470,151 A | * | 9/1969 | Doyle ................. | C07D 499/00 540/337 |
| 5,700,761 A | * | 12/1997 | Kilama ................ | C07D 209/52 504/221 |
| 2007/0105899 A1 | | 5/2007 | Suzuki et al. | |

FOREIGN PATENT DOCUMENTS

| | | |
|---|---|---|
| WO | WO 99/97215 A1 * | 12/1999 |
| WO | 03/049741 | 6/2003 |
| WO | 2005/108352 | 11/2005 |
| WO | 2007/070556 | 6/2007 |
| WO | WO 2009017705 A1 * | 2/2009 |

OTHER PUBLICATIONS

Carey, FA. Organic Chemistry 6th Ed. McGraw Hill. 2006, chapter 1, p. 9.*
Stedman, RJ. et al. Semisynthetic penicillins. II. Structure-activity studies on the 2-biphenylyl side chain. J. Med. Chem. 1964, vol. 7, p. 251.*
International Search Report issued in International Application No. PCT/EP2014/055222, dated May 27, 2014, in 3 pages.

* cited by examiner

*Primary Examiner* — Noble Jarrell
*Assistant Examiner* — Ben S Michelson

(57) ABSTRACT

The invention provides novel compounds having the general formula (I)

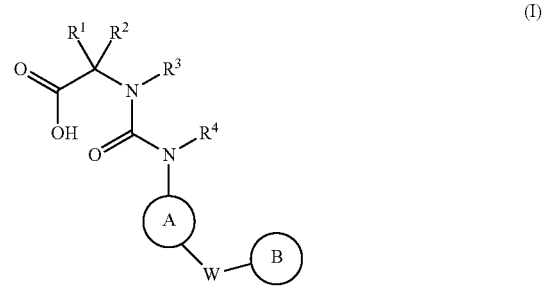

wherein $R^1$, $R^2$, $R^3$, $R^4$, W, A and B are as described herein, compositions including the compounds and methods of using the compounds.

3 Claims, No Drawings

UREA DERIVATIVES AND THEIR USE AS FATTY-ACID BINDING PROTEIN (FABP) INHIBITORS

CROSS-REFERENCE TO RELATED APPLICATIONS

This application is a continuation application of International Application No. PCT/EP2014/055222, filed on Mar. 17, 2014, which claims priority to European Patent Application No. 13160084.3, filed on Mar. 20, 2013, the entire contents of which are incorporated herein by reference.

The present invention relates to organic compounds useful for therapy or prophylaxis in a mammal, and in particular to fatty-acid binding protein (FABP) 4 and/or 5 inhibitors, more particularly dual FABP 4/5 inhibitors for the treatment or prophylaxis of e.g. type 2 diabetes, atherosclerosis, chronic kidney diseases, non-alcoholic steatohepatitis and cancer.

The present invention provides novel compounds of formula (I)

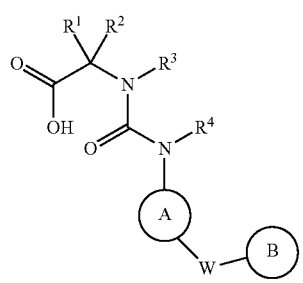

wherein
$R^1$ and $R^3$ together with the carbon and nitrogen atom they are attached to form a heterocycloalkyl;
$R^2$ is H, alkyl, haloalkyl, cycloalkyl, halocycloalkyl, cycloalkylalkyl, halocycloalkylalkyl, phenyl or substituted phenyl, wherein substituted phenyl is substituted with one to three substituent selected from alkyl, hydroxyalkyl, haloalkyl, cycloalkyl, alkoxy, haloalkoxy, halogen, hydroxy and cyano;
$R^4$ is H, alkyl or cycloalkyl;
W is a bond, —O—, —S—, —NR$^5$—, —C(O)—, —S(O)$_2$—, —C(O)—NR$^5$— or —CR$^6$R$^7$—;
$R^5$ is H, alkyl or cycloalkyl;
$R^6$ and $R^7$ are independently selected from H, alkyl or cycloalkyl;
A is substituted phenyl, substituted thiophenyl, substituted benzothiophenyl, substituted thienopyridinyl, wherein substituted phenyl, substituted thiophenyl, substituted benzothiophenyl and substituted thienopyridinyl are substituted with $R^8$, $R^9$ and $R^{10}$;
B is substituted cycloalkyl, substituted cycloalkenyl, substituted pyridinyl, substituted phenyl, substituted thiophenyl, substituted benzothiophenyl, substituted thienopyridinyl, wherein substituted cycloalkyl, substituted cycloalkenyl, substituted pyridinyl, substituted phenyl, substituted thiophenyl, substituted benzothiophenyl and substituted thienopyridinyl are substituted with $R^{11}$, $R^{12}$ and $R^{13}$;
$R^8$, $R^9$, $R^{10}$ are independently selected from H, alkyl, alkenyl, alkinyl, hydroxyalkyl, haloalkyl, hydroxyhaloalkyl, cycloalkyl, cycloalkenyl, cycloalkylalkyl, cycloalkenylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, phenyl, substituted phenyl, pyridinyl, substituted pyridinyl, halogen, hydroxy, cyano, substituted aminosulfonyl, substituted aminocarbonyl, substituted amino and substituted aminoalkyl, wherein substituted aminosulfonyl, substituted aminocarbonyl, substituted amino and substituted aminoalkyl are substituted on the nitrogen atom with one to two substituents independently selected from hydrogen, alkyl, cycloalkyl, cycloalkylalkyl, hydroxyalkyl, alkoxyalkyl, alkylcarbonyl and cycloalkylcarbonyl and wherein substituted phenyl and substituted pyridinyl are substituted with one to three substituent selected from alkyl, hydroxyalkyl, haloalkyl, cycloalkyl, alkoxy, haloalkoxy, halogen, hydroxy and cyano;
$R^{11}$, $R^{12}$ and $R^{13}$ are independently selected from H, alkyl, alkenyl, alkinyl, hydroxyalkyl, haloalkyl, hydroxyhaloalkyl, cycloalkyl, cycloalkenyl, cycloalkylalkyl, cycloalkenylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, phenyl, substituted phenyl, pyridinyl, substituted pyridinyl, halogen, hydroxy, cyano, substituted aminosulfonyl, substituted aminocarbonyl, substituted amino and substituted aminoalkyl, wherein substituted aminosulfonyl, substituted aminocarbonyl, substituted amino and substituted aminoalkyl are substituted on the nitrogen atom with one to two substituents independently selected from hydrogen, alkyl, cycloalkyl, cycloalkylalkyl, hydroxyalkyl, alkoxyalkyl, alkylcarbonyl and cycloalkylcarbonyl and wherein substituted phenyl and substituted pyridinyl are substituted with one to three substituent selected from alkyl, hydroxyalkyl, haloalkyl, cycloalkyl, alkoxy, haloalkoxy, halogen, hydroxy and cyano;
or pharmaceutically acceptable salts;
with the proviso that CAS 1080643-64-6 is excluded.

FABP4 (aP2) and FABP5 (mal1) are members of the fatty acid binding protein family. FABPs are proteins of 14-15 KDa that act as chaperones for fatty acids in the aqueous cytosolic environment and facilitate their movement between cellular compartments. So far at least nine members of this family have been identified with a tissue-specific pattern of expression. FABP4 is mainly expressed in adipose and macrophages, but also in other cell types, whereas FABP5 is expressed in a wide range of tissues and organs. FABPs are responsible for the transfer of fatty acids to different cell compartments and are thus implicated in key cellular functions such as lipid storage in adipocytes, fatty acid oxidation in mitochondria, ER signaling, fatty-acid-dependent gene expression, regulation of cytosolic enzymes activity, modulation of inflammatory response and leukotrienes synthesis. Plasma FABP4 is secreted by adipose tissue in mice and secretion is de-regulated in obesity and blocking of plasma FABP4 in vivo by antibodies improves insulin sensitivity.

Several genetic evidences in human support a role of FABP4 and FABP5 in metabolic diseases. A mutation in the FABP4 promoter (SNP T-87C) leading to 50% reduction in gene expression is associated to reduced cardiovascular diseases (CVDs) and type 2 diabetes (T2D) risk and to reduced plasma triglycerides (TGs). Two mutations in FABP5 gene, one in the 5'UTR (rs454550), one in the promoter (nSNP), are associated, respectively to increased (OR 4.24) and decreased risk (OR 0.48) of T2D. In addition, it was shown that FABP4 protein and mRNA levels in atherosclerotic plaque macrophages are associated to plaques instability and CV death. Finally, a large number of publications report an association between FABP4 and FABP5 plasma levels and severity of metabolic diseases. Elevated FABP4 plasma levels are associated with atherogenic dyslipidemia, reduced endothelial function, increased intima-media (IM) thickness, metabolic syndrome, obesity and insulin resistance IR. Elevated FABP5 plasma levels are associated to metabolic syndrome.

Genetic and pharmacological studies in mice largely confirm the human evidences. It was demonstrated that loss-of-function in FABP4 and FABP5 improves insulin sensitivity, lowers glucose, and protects against atherosclerosis. FABP4 knockout mice on high fat diet showed metabolic improvement that was tempered by compensatory upregulation of FABP5 in adipose. Mice with a deletion of FABP5 gene on high fat (HF) diet showed body weight reduction and improved glucose and insulin tolerance. The FABP4/FABP5 double-knockout mice were strongly protected from hyperglycemia, insulin resistance, and hepatic steatosis. In addition, in an ApoE deficient background, FABP4 and FABP5 deletion was highly protective against the development of atherosclerosis and increased longevity. A specific FABP4 inhibitor (BMS309403), showed in a clamp study in ob/ob mice a reduction of hepatic glucose production, increased glucose uptake in muscle and adipose and reduction in hepatic steatosis, but no change in body weight and energy consumption. Also, it showed a decrease in atherosclerotic placques formation in ApoE KO mice. A dual FABP4/5 inhibitor Compound 3 described in J. Lipid Res. 2011, 52, 646 showed in mice under HF diet a reduction in plasma triglyceride and free fatty acid, but no improvement in insulin and glucose tolerance.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome, and the use of the said compounds, salts or esters for the production of medicaments for the treatment or prophylaxis of of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome.

Compounds of the present invention are FABP 4 and 5 inhibitors. More particular compounds of formula (I) of the present invention are selective FABP 4 inhibitors compared to FABP 5 and 3 and/or 1.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl is pronenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and isopropoxy. A more particular alkoxy group is methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl and ethoxypropyl. Particular alkoxyalkyl group include methoxymethyl and methoxyethyl. A more particular alkoxyalkyl group is methoxyethyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl groups are methyl and ethyl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, prop-2-ynyl, isopropynyl, n-butynyl, and iso-butyryl.

The term "amino" denotes a —NH$_2$ group.

The term "aminoalkyl" denotes an alkyl group wherein at least one of the hydrogen atoms of the alkyl group has been replaced by an aminogroup. Examples of aminoalkyl include aminomethyl, aminoethyl, amino-1-methyl-ethyl, aminopropyl, aminomethylpropyl and aminopropyl.

The term "aminocarbonyl" denotes a group of the formula —C(O)—NH$_2$.

The term "aminosulfonyl" denotes a —S(O)$_2$—NH$_2$ group.

The term "cyano" denotes a —C≡N group.

The term "cycloalkenyl" denotes a monovalent unsaturated non-aromatic monocyclic or bicyclic hydrocarbon group of 3 to 8 ring carbon atoms. Particular cycloalkenyl groups are monocyclic. Examples of cycloalkenyl groups include cyclobutenyl, cyclopentenyl and cyclohexenyl. Particular cycloalkenyl is cyclohexenyl.

The term "cycloalkenylalkyl" denotes an alkyl group wherein at least one of the hydrogen atoms of the alkyl group is replaced by a cycloalkenyl group. Examples of cycloalkenylalkyl include cyclobutenylmethyl, cyclopentenylmethyl and cyclohexenylmethyl.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated or partially saturated carbocycles having two carbon atoms in common. Particular cycloalkyl groups are cyclopropyl, cyclobutyl, cyclopentyl, cyclohexyl, cycloheptanyl, bicyclo[2.2.2]heptanyl, bicyclo[2.2.2]octanyl, substituted bicyclo[2.2.2]heptanyl and substituted bicyclo[2.2.2]octanyl. Further particular cycloalkyl groups are cyclopropyl, cyclobutyl and cyclopentyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group is trifluoromethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo, or iodo. Particular halogens are chloro and fluoro.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular examples are hydroxymethyl and hydroxyethyl.

The term "hydroxyhaloalkyl" denotes a haloalkyl group wherein at least one of the hydrogen atoms of the haloalkyl group has been replaced by an hydroxy group. Exemplary hydroxyhaloalkyl groups include hydroxytrifluoroethyl and hydroxytrifluoropropyl. Particular hydroxyhaloalkyl groups include hydroxytrifluoroethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts. Particular pharmaceutically acceptable salts of compounds of formula (I) are also the sodium and potassium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

CAS 1080643-64-6 means 1-(Biphenyl-4-ylcarbamoyl)-pyrrolidine-2-carboxylic acid.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ and $R^3$ together with the carbon and nitrogen atom they are attached to form a azetidinyl, a pyrrolidinyl, a piperidinyl, a thiazolidinyl or a 3-aza-bicyclo[3.1.0]hexyl.

A more particular embodiment of the present invention are compounds according to formula (I) as described herein, wherein $R^1$ and $R^3$ together with the carbon and nitrogen atom they are attached to form a azetidinyl.

A particular embodiment of the present invention are compounds according to formula (I) as described herein, wherein $R^2$ is H, alkyl or phenyl.

A particular embodiment of the present invention are compounds according to formula (I) as described herein, wherein $R^2$ is H.

A particular embodiment of the present invention are compounds according to formula (I) as described herein, wherein $R^4$ is H.

In a further embodiment of the present invention are compounds according to formula (I) as described herein, wherein W is a bond, —O— or —$CR^6R^7$—.

Another further embodiment of the present invention are compounds according to formula (I) as described herein, wherein W is a bond.

Another embodiment of the present invention are compounds according to formula (I) as described herein, wherein $R^6$ and $R^7$ are H.

A further embodiment of the present invention are compounds according to formula (I) as described herein, wherein A is substituted phenyl, substituted thiophenyl, substituted benzothiophenyl, substituted thienopyridinyl, wherein substituted phenyl, substituted thiophenyl, substituted benzothiophenyl and substituted thienopyridinyl are substituted with $R^8$, $R^9$ and $R^{10}$.

Another particular embodiment of the present invention are compounds according to formula (I) as described herein, wherein A is phenyl substituted with $R^8$, $R^9$ and $R^{10}$.

The present invention also relates to compounds according to formula (I) as described herein, wherein A is 4-chlorophenyl.

A further particular embodiment of the present invention are compounds according to formula (I) as described herein, wherein B is substituted cycloalkenyl, substituted pyridinyl, substituted phenyl, substituted thiophenyl, substituted benzothiophenyl, substituted thienopyridinyl, wherein substituted cycloalkenyl, substituted pyridinyl, substituted phenyl, substituted thiophenyl, substituted benzothiophenyl and substituted thienopyridinyl are substituted with $R^{11}$, $R^{12}$ and $R^{13}$.

A more particular embodiment of the present invention are compounds according to formula (I) as described herein, B is 4-fluorophenyl.

A more particular embodiment of the present invention are compounds according to formula (I) as described herein, wherein $R^8$ is halogen and $R^9$ and $R^{10}$ are H.

A further particular embodiment of the present invention are compounds according to formula (I) as described herein, wherein $R^{11}$ is H or halogen and $R^{12}$ and $R^{13}$ are H.

A more particular embodiment of the present invention are compounds according to formula (I) as described herein, wherein $R^1$ and $R^3$ together with the carbon and nitrogen atom they are attached to form a azetidinyl and of formula (Ia).

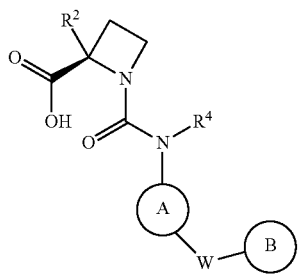

(Ia)

Particular examples of compounds of formula (I) as described herein are selected from 1-(Biphenyl-2-ylcarbamoyl)-piperidine-2-carboxylic acid;
(R)-1-(5-chlorobiphenyl-2-ylcarbamoyl)pyrrolidine-2-carboxylic acid;
(R)-1-(2-phenoxyphenylcarbamoyl)pyrrolidine-2-carboxylic acid;
(R)-1-(2-benzylphenylcarbamoyl)pyrrolidine-2-carboxylic acid;
(R)-1-(5-chloro-2-phenoxyphenylcarbamoyl)pyrrolidine-2-carboxylic acid;
1-(Biphenyl-2-ylcarbamoyl)-2-phenyl-pyrrolidine-2-carboxylic acid;
3-(Biphenyl-2-ylcarbamoyl)-thiazolidine-2-carboxylic acid;
(S)-3-(Biphenyl-2-ylcarbamoyl)-thiazolidine-4-carboxylic acid;
(1SR,2SR,5RS)-3-(Biphenyl-2-ylcarbamoyl)-3-aza-bicyclo[3.1.0]hexane-2-carboxylic acid;
(R)-1-(4-chlorobiphenyl-2-ylcarbamoyl)pyrrolidine-2-carboxylic acid;
(R)-1-(3-fluorobiphenyl-2-ylcarbamoyl)pyrrolidine-2-carboxylic acid;
(R)-1-(4-chlorobiphenyl-2-ylcarbamoyl)azetidine-2-carboxylic acid;
(R)-1-(4-(trifluoromethyl)biphenyl-2-ylcarbamoyl)pyrrolidine-2-carboxylic acid;
(R)-1-(4,6-difluorobiphenyl-2-ylcarbamoyl)pyrrolidine-2-carboxylic acid;
1-(biphenyl-2-ylcarbamoyl)-2-methylpyrrolidine-2-carboxylic acid;
(R)-1-(4-fluorobiphenyl-2-ylcarbamoyl)pyrrolidine-2-carboxylic acid;
(R)-1-(4-(trifluoromethoxy)biphenyl-2-ylcarbamoyl)pyrrolidine-2-carboxylic acid;
(R)-1-(4,6-dichlorobiphenyl-2-ylcarbamoyl)pyrrolidine-2-carboxylic acid;
(R)-1-(5'-Chloro-[1,1';2',1"]terphenyl-3'-ylcarbamoyl)-pyrrolidine-2-carboxylic acid;
(R)-1-(4-cyanobiphenyl-2-ylcarbamoyl)pyrrolidine-2-carboxylic acid;
(R)-1-(2-phenylbenzo[b]thiophen-3-ylcarbamoyl)pyrrolidine-2-carboxylic acid;
(R)-1-(2-phenylthieno[2,3-b]pyridin-3-ylcarbamoyl)pyrrolidine-2-carboxylic acid;
(R)-1-(6-allyl-4-chlorobiphenyl-2-ylcarbamoyl)pyrrolidine-2-carboxylic acid;
(R)-1-(2-phenylthiophen-3-ylcarbamoyl)pyrrolidine-2-carboxylic acid;
(R)-1-(4-chloro-6-cyanobiphenyl-2-ylcarbamoyl)pyrrolidine-2-carboxylic acid;
(R)-1-[4-chloro-6-(cyclohexen-1-yl)-biphenyl-2-ylcarbamoyl]pyrrolidine-2-carboxylic acid;
(S)-1-(4-chlorobiphenyl-2-ylcarbamoyl)azetidine-2-carboxylic acid;
(R)-1-(biphenyl-2-ylcarbamoyl)azetidine-2-carboxylic acid;
(R)-1-(4-chloro-4'-fluorobiphenyl-2-ylcarbamoyl)azetidine-2-carboxylic acid;
(R)-1-(4-chloro-5-fluorobiphenyl-2-ylcarbamoyl)azetidine-2-carboxylic acid;
(R)-1-(4-chloro-5-methylbiphenyl-2-ylcarbamoyl)azetidine-2-carboxylic acid;
(R)-1-(4-chloro-2',3'-difluorobiphenyl-2-ylcarbamoyl)azetidine-2-carboxylic acid;
(R)-1-(4-chloro-2'-fluorobiphenyl-2-ylcarbamoyl)azetidine-2-carboxylic acid;
(R)-1-(4-chloro-3'-fluorobiphenyl-2-ylcarbamoyl)azetidine-2-carboxylic acid;
(R)-1-(4-chloro-3',5'-difluorobiphenyl-2-ylcarbamoyl)azetidine-2-carboxylic acid;
(R)-1-(5-chloro-2-(thiophen-3-yl)phenylcarbamoyl)pyrrolidine-2-carboxylic acid;
(R)-1-(2-(benzo[b]thiophen-3-yl)-5-chlorophenylcarbamoyl)pyrrolidine-2-carboxylic acid;
(R)-1-(4-chloro-4'-fluorobiphenyl-2-ylcarbamoyl)pyrrolidine-2-carboxylic acid;
(R)-1-(3',4-dichlorobiphenyl-2-ylcarbamoyl)pyrrolidine-2-carboxylic acid;
(R)-1-(3'-carbamoyl-4-chlorobiphenyl-2-ylcarbamoyl)pyrrolidine-2-carboxylic acid;
(R)-1-[5-chloro-2-(cyclohexen-1-yl)phenylcarbamoyl]pyrrolidine-2-carboxylic acid;
(R)-1-(5-chloro-2-(pyridin-4-yl)phenylcarbamoyl)pyrrolidine-2-carboxylic acid;
(R)-1-(4,4'-dichlorobiphenyl-2-ylcarbamoyl)pyrrolidine-2-carboxylic acid;
(R)-1-(4-chloro-4'-methoxybiphenyl-2-ylcarbamoyl)pyrrolidine-2-carboxylic acid;
(R)-1-(4-chloro-2'-methylbiphenyl-2-ylcarbamoyl)pyrrolidine-2-carboxylic acid;
(R)-1-(4-ethylbiphenyl-2-ylcarbamoyl)pyrrolidine-2-carboxylic acid;
(R)-1-(4-chloro-2',4'-difluorobiphenyl-2-ylcarbamoyl)azetidine-2-carboxylic acid;
(R)-1-(4-chloro-4'-fluoro-6-methoxybiphenyl-2-ylcarbamoyl)azetidine-2-carboxylic acid;
and pharmaceutically acceptable salts thereof.

Further particular examples of compounds of formula (I) as described herein are selected from
(R)-1-(4-chlorobiphenyl-2-ylcarbamoyl)azetidine-2-carboxylic acid;
(R)-1-(4-chloro-4'-fluorobiphenyl-2-ylcarbamoyl)azetidine-2-carboxylic acid;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the person skilled in the art such as, e.g. chiral chromatography or crystallization. In case one of the starting materials or compounds of formula (I) contain one or more functional groups which are not stable or are reactive under the reaction conditions of one or more reaction steps, appropriate protecting groups can be introduced before the critical step applying methods well known in the art. Such protecting groups can be removed at a later stage of the synthesis using standard methods described in the literature. The substituents and indices used in the following description of the processes have the significance given herein.

Compounds of formula (I), wherein $R^4$ is H may be prepared as illustrated in Scheme 1.

Scheme 1

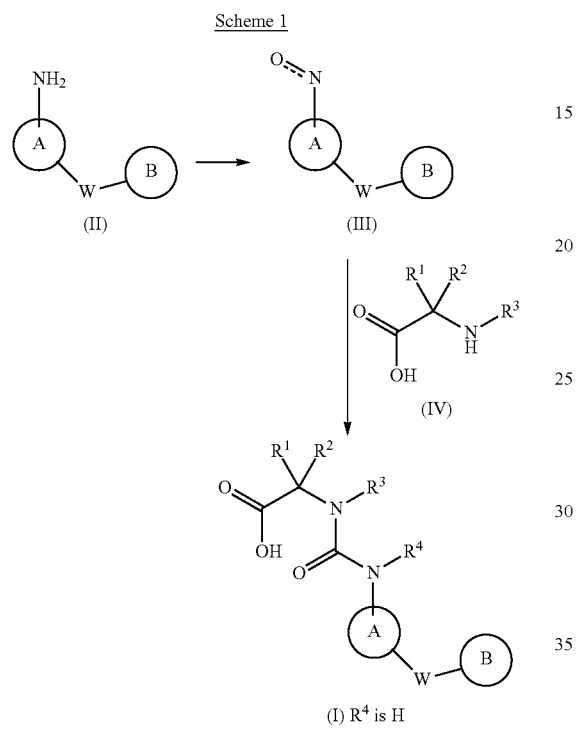

(I) $R^4$ is H

An amino compound (II) can be converted to an isocyanate (III) by methods well known in the art, e.g. by treatment with phosgene or a synthetic equivalent of phosgene such as triphosgene in the presence of a base such as triethylamine in a solvent such as toluene, dichloromethane or tetrahydrofuran. The isocyanate (III) can be reacted with an amino acid (IV) in the presence of a base such as triethylamine in a solvent such as dichloromethane to give a urea (I), wherein $R^4$ is H.

An alternative synthesis for compounds of formula (I), wherein $R^4$ is H is illustrated in Scheme 2.

Scheme 2

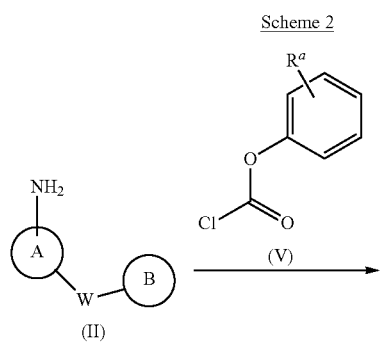

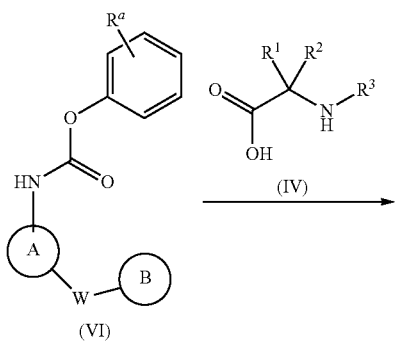

(VI)

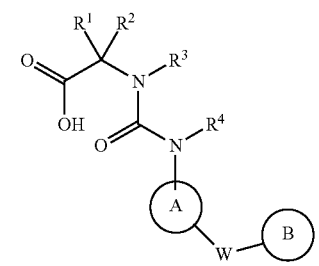

(I) $R^4$ is H $R^a$ is H or a functional group, e.g. NO2 or F

An amino compound (II) can be converted to an arylcarbamate (VI) such as a phenylcarbamate by methods well known in the art, e.g. by treatment with an arylchloroformate (V) such as phenylchloroformate, optionally in the presence of a base such as triethylamine or pyridine in a solvent such as tetrahydrofuran or toluene at a temperature from room temperature to reflux of the solvent. The arylcarbamate (VI) can be reacted with an amino acid (IV) in the presence of a base such as potassium carbonate or triethylamine in a solvent or a solvent mixture such as water, tetrahydrofuran, toluene or N,N-dimethylformamide at a temperature from room temperature to reflux of the solvent to give a urea (I), wherein $R^4$ is H.

Compounds (I), wherein $R^4$ is H and W is a bond can be alternatively prepared as described in Scheme 3:

Scheme 3

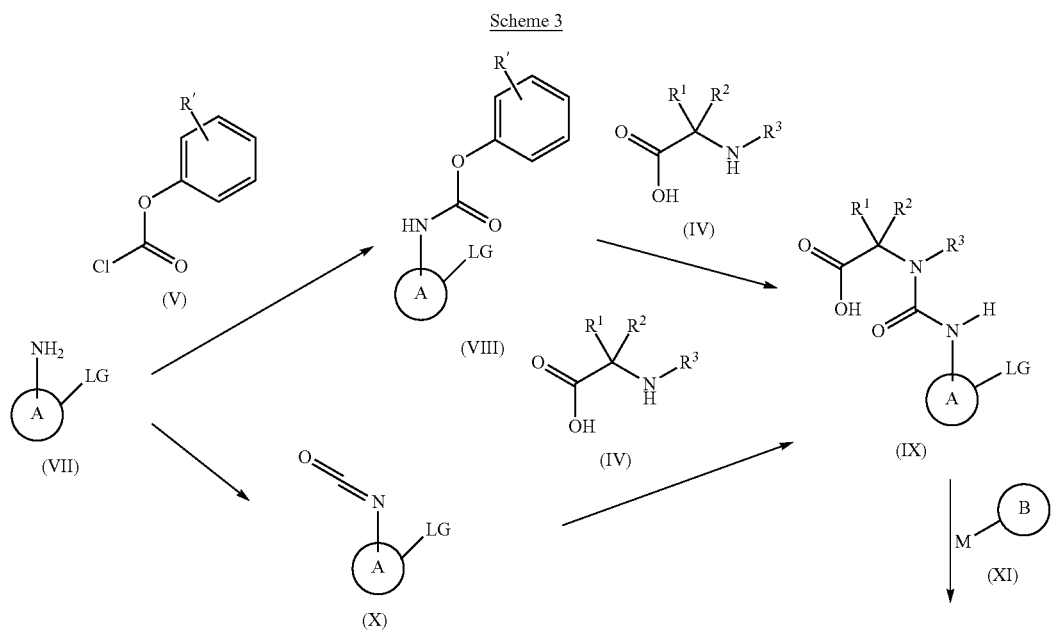

LG is a leaving group, e.g. Br, Cl, I, —OSO$_2$CF$_3$
R' is H or a functional group, e.g. NO$_2$, F
M is a metal derivative, e.g. boronic acid, a boronic acid derivative, —SnBu$_3$ An amine (VII) containing a leaving group such as Br, Cl, I, —OSO$_2$CF$_3$ can be converted to an arylcarbamate (VIII) followed by reaction with an amino acid (IV) to give the urea (IX) using the methods illustrated in Scheme 2. Alternatively, urea (IX) may be prepared from the amine (VII) by conversion into the isocyanate (X) followed by reaction with the amino acid (IV) using the methods described in Scheme 1.

Ureas (IX) can be converted into a compound (I) in which W is a bond and $R^4$ is H by palladium catalyzed coupling with suitable metal derivatives such as boronic acids, boronic acid derivatives or trialkyl tin derivatives in the presence of a suitable catalyst such as dichloro(1,1'-bis(diphenylphosphino)ferrocene)palladium(II)dichloromethane adduct.

Compounds (I) in which $R^4$ is alkyl or cycloalkyl may be prepared as illustrated in Scheme 4:

Scheme 4

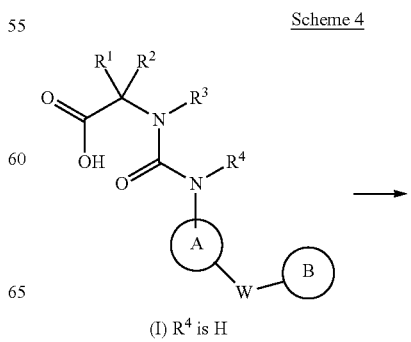

(I) $R^4$ is H

-continued

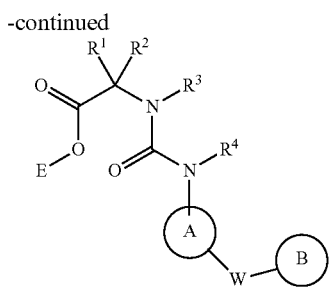

(XII) R⁴ is H and E is Me, Et or t-Bu

↓

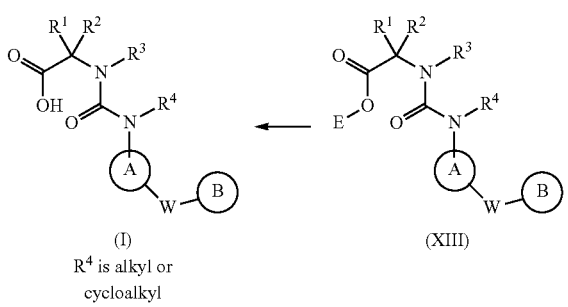

(I) R⁴ is alkyl or cycloalkyl       (XIII)

The carboxylic acid of a compound (I) in which R⁴ is H can be protected as an ester such as a methyl, ethyl or t-butyl ester by using methods well known in the art. The obtained ester (XII) can be reacted with an alkylating agent such as an alkyl or cycloalkyl halide or triflate in the presence of a base such as potassium carbonate or triethylamine in a solvent such as tetrahydrofuran or N,N-dimethylformamide. The alkylated product (XIII) can be purified by using chromatographic methods known by persons skilled in the art. The compound (I) in which R⁴ is alkyl or cycloalkyl can be obtained from compound (XIII) by cleavage of the ester using methods described in the literature and known by persons skilled in the art.

Also an embodiment of the present invention is a process to prepare a compound of formula (I) as defined above comprising the reaction of a compound of formula (III) in the presence of a compound of formula (IV);

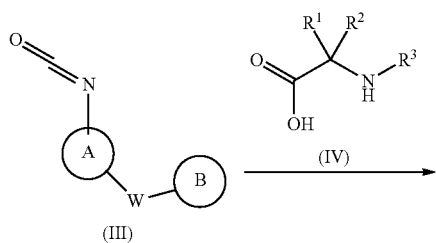

(III)

-continued

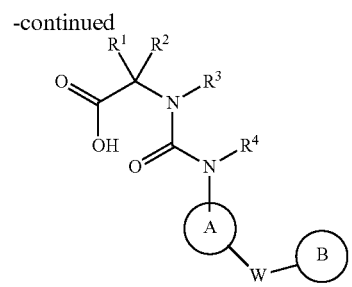

(I)

wherein $R^1$, $R^2$, $R^3$, A, B and W are as defined above and wherein $R^4$ is H.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

In accordance with the invention, the compounds of formula (I) or their pharmaceutically acceptable salts and esters can be used for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Particular liver diseases are liver diseases involving inflammation, steatosis and/or fibrosis, such non-alcoholic fatty liver disease, more particularly non-alcoholic steatohepatitis.

Particular lipodystrophy is genetic and iatrogenic lipodystrophy.

Particular eye diseases are eye diseases supported by endothelial proliferation and angiogenesis, particularly macular degeneration and retinopathy.

Particular lung diseases are asthma, bronchopulmonary dysplasia and chronic obstructive pulmonary disease.

Particular chronic renal diseases are vasculitis, focal segmental glomerulosclerosis, diabetic nephropathy, lupus nephritis, polycystic kidney disease and drug or toxin-induced chronic tubulointerstitial nephritis.

The present invention also relates to the use of a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the treatment or prophylaxis of type 2 diabetes, atherosclerosis, cancer, chronic renal disease and non-alcoholic steatohepatitis.

The present invention also relates to the use of a compound according to formula (I) as described herein for the treatment or prophylaxis of non-alcoholic steatohepatitis.

A particular embodiment of the present invention is a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Another particular embodiment of the present invention is a compound according to formula (I) as described herein for the treatment or prophylaxis of type 2 diabetes, atherosclerosis, cancer, chronic renal disease and non-alcoholic steatohepatitis.

Also a particular embodiment of the present invention is a compound according to formula (I) as described herein for the treatment or prophylaxis of non-alcoholic steatohepatitis.

The present invention also relates to the use of a compound according to formula (I) as described herein for the preparation of a medicament for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the preparation of a medicament for the treatment or prophylaxis of type 2 diabetes, atherosclerosis, cancer, chronic renal disease and non-alcoholic steatohepatitis.

Also an embodiment of the present invention is the use of a compound according to formula (I) as described herein for the preparation of a medicament for the treatment or prophylaxis of non-alcoholic steatohepatitis.

Also an object of the invention is a method for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome, which method comprises administering an effective amount of a compound according to formula (I) as described herein.

Another object of the invention is a method for the treatment or prophylaxis of type 2 diabetes, atherosclerosis, cancer, chronic renal disease and non-alcoholic steatohepatitis, which method comprises administering an effective amount of a compound according to formula (I) as described herein.

Also an embodiment of the present invention is a method for the treatment or prophylaxis of non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also a particular embodiment of the present invention is a compound according to formula (I) as described herein, when manufactured according to any one of the described processes.

Assay Procedures

Compounds were profiled for activity against human FABP4 (huFABP4) and/or human FABP5 (huFABP5) in Terbium (Tb) time resolved-fluorescence energy transfer (TR-FRET) assays monitoring the direct binding of Bodipy labeled fatty acid to His6 tagged FABP proteins (huFABP4 was expressed in house in *E. coli* and purified, huFABP5 was purchased from Cayman Chemical Co., cat. no. 10010364), bound to Terbium labeled anti His6 tag antibody. Assay read-outs reflected energy transfer, upon binding of the ligand to the FABP protein, from the Terbium donor molecule to the acceptor Bodipy moiety. Final ligand concentration (125 nM) approximated the Kd for each protein.

Stock DMSO solutions (1.8 mM) of compounds were serially diluted 3-fold for ten concentrations with 100% DMSO (50 μM to 0.003 μM final compound concentration). 1 μl of these compound dilutions and 1 μl of Bodipy labeled fatty acid 4.5 μM in 100% DMSO (Bodipy FL C11, cat. no. D3862, Invitrogen) were sequentially pipetted in wells of 384-well black polypropylene plates (Thermo Matrix cat. no. 4344). FABP4 or FABP5 protein was then added (28 μl of 64 nM protein in 25 mM Tris pH 7.5, 0.4 mg/ml γ-globulin, 1 mM DTT, 0.012% NP40, final protein concentration: 50 nM). Assay blanks contained ligand, but no protein. Neutral controls contained ligand, but no compound. After adding the detection reagent (Tb antiHis6 antibody, Columbia Biosciences, TB-110, 6 μl of a 24 nM Ab solution in 25 mM Tris pH 7.5, 0.4 mg/ml γ-globulin, final Tb antiHis6 Ab concentration: 4 nM), plates were spun one minute at 1000 rpm. Following an incubation at room temperature with shaking for 30 minutes, plates were read using an Envision reader (Perkin Elmer, Extinction wavelength: 340 nm, Emission: 490 nm and 520 nm, time delay: 100 μs; time window: 200 μs, 50 flashes).

Final assay conditions were: 50 nM FABP protein, 125 nM Bodipy labeled fatty acid, 0.009% (vol/vol) NP40, 5.5% (vol/vol) DMSO in a total final assay volume of 36 μl. The assay was performed in triplicate.

The relative fluorescence units (RFU) ratio (520 nm*10000/488 nm) were used to calculate the percent inhibition: 100−(RFU ratio compound−blank)/neutral control−blank)*100. These percent inhibition values were then fit to dose response curves using a 4 parameter logistic model (Hill sigmoidal dose-response model). $IC_{50}$s reflected compound concentrations associated with 50% inhibition of protein activity compared to that of neutral controls.

| Example | IC50 h-fabp4-ecoli-r μM | IC50 h-fabp5-ecoli-r μM |
| --- | --- | --- |
| 1 | 8.06 | >50 |
| 2 | 2.04 | 20.96 |
| 3 | 11.66 | >50 |
| 4 | 3.34 | >50 |
| 5 | 7.41 | >50 |
| 6 | 0.62 | >50 |
| 7 | 9.82 | >50 |
| 8 | 0.33 | >50 |
| 9 | 9.1 | >50 |
| 10 | 0.12 | >1.44 |
| 11 | 0.86 | >50 |
| 12 | 0.02 | >50 |
| 13 | 3.95 | >50 |
| 14 | 0.31 | >6.86 |
| 15 | 0.86 | >50 |
| 16 | 1.07 | >50 |
| 17 | 5.71 | >50 |
| 18 | 0.11 | 18.17 |
| 19 | 0.5 | 1.22 |
| 20 | 10.48 | >50 |
| 21 | 0.67 | >50 |
| 22 | 1.66 | >50 |
| 23 | 0.11 | 1.29 |
| 24 | 1.67 | >50 |
| 25 | 0.19 | 14.99 |
| 26 | 0.53 | 0.07 |
| 27 | 1.22 | >50 |
| 28 | 0.08 | >50 |

-continued

| Example | IC50<br>h-fabp4-ecoli-r<br>μM | IC50<br>h-fabp5-ecoli-r<br>μM |
|---|---|---|
| 29 | 0.03 | >50 |
| 30 | 0.02 | 40.07 |
| 31 | 0.03 | 5.08 |
| 36 | 0.06 | >50 |
| 37 | 0.03 | >50 |
| 38 | 0.03 | >50 |
| 39 | 0.06 | >50 |
| 52 | 0.06 | >10.36 |
| 53 | 0.34 | 42.23 |
| 54 | 0.06 | >29.55 |
| 55 | 0.77 | >50 |
| 56 | 11.07 | >50 |
| 57 | 1.1 | >50 |
| 58 | 2 | >50 |
| 59 | 2.08 | >50 |
| 60 | 3.45 | >50 |
| 61 | 2.75 | >50 |
| 62 | 1.86 | >50 |
| 63 | 0.03 | >50 |
| 64 | 0.02 | 6.66 |

Compounds of formula (I) and their pharmaceutically acceptable salts or esters thereof as described herein have $IC_{50}$ (FABP4 inhibition) values between 0.000001 μM and 1000 μM, particular compounds have $IC_{50}$ values between 0.000005 μM and 500 μM, further particular compounds have $IC_{50}$ values between 0.00005 μM and 5 μM.

Compounds of formula (I) and their pharmaceutically acceptable salts or esters thereof as described herein have $IC_{50}$ (FABP5 inhibition) values between 0.000001 μM and 1000 μM, particular compounds have $IC_{50}$ values between 0.000005 μM and 500 μM, further particular compounds have $IC_{50}$ values between 0.00005 μM and 50 μM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases.

The invention is illustrated hereinafter by Examples, which have no limiting character.

In case the preparative examples are obtained as a mixture of enantiomers, the pure enantiomers can be separated by methods described herein or by methods known to the person skilled in the art, such as e.g. chiral chromatography or crystallization.

EXAMPLES

All examples and intermediates were prepared under argon atmosphere if not specified otherwise.

General Method A: Synthesis of an Isocyanate from an Aniline

To a solution of the aniline (5.21 mmol, 1.00 equivalent) in toluene (19.0 ml), triphosgene (0.35 equivalents) is added slowly and the reaction mixture is heated to reflux for 1 h. The reaction mixture is concentrated to dryness and the product is either purified by bulb-to-bulb distillation or used in the next step without further purification.

General Method B: Synthesis of a Urea from an Isocyanate

To a suspension of the aminoacid (1.48 mmol, 1 equivalent) in DCM (4 ml) are added triethylamine (1 equivalent) and the isocyanate (1 equivalent). The reaction mixture is stirred at r.t. for 5 to 36 h. Half-concentrated aqueous sodium carbonate solution is added. The layers are separated and the aqueous layer is washed with DCM. The organic layer is extracted with diluted sodium carbonate solution. The combined aqueous layers are acidified with concentrated hydochloric acid. If the product precipitates, it can be collected by filtration and dried. In case the product does not precipitate it can be obtained by extraction with DCM. The organic layers are dried over $Na_2SO_4$, filtered and concentrated to dryness. If desired, the product can be further purified by chromatography.

General Method C: Synthesis of a Urea from an Aniline Via Carbamate-Intermediate A solution of the aniline (2.09 mmol, 1.00 equivalent) in THF (4.0 ml) is cooled in an ice bath. A solution of phenyl chloroformate (1.04 equivalents) in THF (3.01 ml) is added. The reaction mixture is heated to reflux for 1 to 4 h. After cooling to r.t., the amino acid (1.1 equivalents), potassium carbonate (3 equivalents) and water (5.26 ml) are added. The reaction mixture is stirred at r.t. for 18 to 36 h. The mixture is diluted with water and washed with n-heptane. The aqueous layer is partially evaporated to remove organic solvents. At r.t., the aqueous layer is slowly acidified using 25% HCl. The precipitated product can be collected by filtration, washed with little water and dried. In case the product does not precipitate it can be obtained by extraction with DCM. The organic layers are dried over Na$_2$SO$_4$, filtered and concentrated to dryness. If desired, the product can be further purified by chromatography.

General Method D: Suzuki Coupling

An aromatic bromide, iodide, triflate or mesylate (0.29 mmol, 1 equivalent), a boronic acid or boronic acid ester (1.5 equivalents) and a 2 M aqueous solution of sodium carbonate (3 equivalents) are combined under argon with dioxane (3.5 ml) and water (1.4 ml). [1,1'-Bis(diphenylphosphino)ferrocene]dichloropalladium(II), dichloromethane adduct (0.05 equivalents) is added and the reaction mixture is stirred at 80° C. for 3 to 10 h. After cooling to r.t., the mixture is filtered. Diluted aqueous HCl is added and the mixture is extracted with EtOAc. The combined organic layers are dried over MgSO$_4$, filtered and concentrated in vacuo. The product can be purified by chromatography.

| Example | Name / Structure / MS | Method | Reagents |
|---|---|---|---|
| 1 | (RS)-1-(biphenyl-2-ylcarbamoyl)-piperidine-2-carboxylic acid<br><br>ESN [M − H]$^-$: 323 | B | 2-piperidinecarboxylic acid (CAS# 4043-87-2); 2-biphenylisocyanate (CAS# 17337-13-2) |
| 2 | (R)-1-(5-chlorobiphenyl-2-ylcarbamoyl)pyrrolidine-2-carboxylic acid<br><br>ESN [M − H]$^-$: 342.9 | A, B | R-proline (CAS# 344-25-2); 5-chlorobiphenyl-2-amine (CAS# 73006-78-7) |
| 3 | (R)-1-(2-phenoxyphenyl-carbamoyl)pyrrolidine-2-carboxylic acid<br><br>ESN [M − H]$^-$: 325.4 | B | R-proline (CAS# 344-25-2); 2-phenoxyphenyl isocyanate (CAS# 59377-20-7) |

-continued

| Example | Name / Structure / MS | Method | Reagents |
|---|---|---|---|
| 4 | (R)-1-(2-benzylphenyl-carbamoyl)pyrrolidine-2-carboxylic acid<br><br>ESN [M − H]⁻: 323.2 | B | R-proline (CAS# 344-25-2): 2-benzylphenyl isocyanate (CAS# 146446-96-0) |
| 5 | (R)-1-(5-chloro-2-phenoxyphenyl-carbamoyl)pyrrolidine-2-carboxylic acid<br><br>ESN [M − H]⁻: 359.1 | B | R-proline (CAS# 344-25-2); 5-chloro-2-phenoxyphenyl isocyanate (CAS# 85385-33-7) |
| 6 | (RS)-1-(biphenyl-2-ylcarbamoyl)-2-phenyl-pyrrolidine-2-carboxylic acid<br><br>ESN [M − H]⁻: 385.3 | B | 2-phenylpyrrolidine-2-carboxylic acid (CAS# 25860-44-0): 2-biphenylisocyanate (CAS# 17337-13-2) |
| 7 | (RS)-3-(biphenyl-2-ylcarbamoyl)-thiazolidine-2-carboxylic acid<br><br>ESN [M − H]⁻: 327.0 | B | thiazolidine-2-carboxylic acid (CAS# 16310-13-7); 2-biphenylisocyanate (CAS# 17337-13-2) |

| Example | Name / Structure / MS | Method | Reagents |
|---|---|---|---|
| 8 | (S)-3-(biphenyl-2-ylcarbamoyl)-thiazolidine-2-carboxylic acid<br><br>ESN [M − H]⁻: 327.0 | B | (S)-thiazolidine-4-carboxylic acid (CAS# 45521-09-3); 2-biphenylisocyanate (CAS# 17337-13-2) |
| 9 | (1SR,2SR,5RS)-3-(biphenyl-2-ylcarbamoyl)-3-aza-bicyclo[3.1.0]hexane-2-carboxylic acid<br><br>ESN [M − H]⁻: 321.1 | B | (1SR,2SR,5RS)-3-azabicyclo[3.1.0]hexane-2-carboxylic acid (CAS# 72029-78-8); 2-biphenylisocyanate (CAS# 17337-13-2) |
| 10 | (R)-1-(4-chlorobiphenyl-2-ylcarbamoyl)pyrrolidine-2-carboxylic acid<br><br>ESN [M − H]⁻: 343.0 | A, B | R-proline (CAS# 344-25-2); 2-amino-4-chlorobiphenyl (CAS# 90-48-2) |
| 11 | (R)-1-(3-fluorobiphenyl-2-ylcarbamoyl)pyrrolidine-2-carboxylic acid<br><br>ESN [M − H]⁻: 327.4 | A, B | R-proline (CAS# 344-25-2); 3-fluoro-[1,1'-biphenyl]-2-amine (CAS# 920752-43-8) |

-continued

| Example | Name / Structure / MS | Method | Reagents |
|---|---|---|---|
| 12 | (R)-1-(4-chlorobiphenyl-2-ylcarbamoyl)azetidine-2-carboxylic acid<br><br>ESN [M − H]⁻: 329.0 | A, B | (R)-azetidine-2-carboxylic acid (CAS# 7729-30-8); 2-amino-4-chlorobiphenyl (CAS# 90-48-2) |
| 13 | (R)-1-(4-trifluoromethyl)biphenyl-2-ylcarbamoyl)pyrrolidine-2-carboxylic acid<br><br>ESN [M − H]⁻: 377.0 | A, B | R-proline (CAS# 344-25-2); 4-(trifluoromethyl)biphenyl-2-amine (CAS# 363-08-6) |
| 14 | (R)-1-(4,6-difluorobiphenyl-2-ylcarbamoyl)pyrrolidine-2-carboxylic acid<br><br>ESP [M + H]⁺: 347.1 | A, B | R-proline (CAS# 344-25-2); 4,6-difluorobiphenyl-2-amine (Intermediate I14) |
| 15 | (RS)-1-(biphenyl-2-ylcarbamoyl)-2-methylpyrrolidine-2-carboxylic acid<br><br>ESP [M + H]⁺: 325.2 | B | 2-methylpyrrolidine-2-carboxylic acid (CAS# 16277-06-8); 2-biphenylisocyanate (CAS# 17337-13-2) |

-continued

| Example | Name / Structure / MS | Method | Reagents |
|---|---|---|---|
| 16 | (R)-1-(4-fluorobiphenyl-2-ylcarbamoyl)pyrrolidine-2-carboxylic acid<br><br>ESN [M − H]⁻: 327.1 | A, B | R-proline (CAS# 344-25-2); 4-fluorobiphenyl-2-amine (CAS# 321-68-6) |
| 17 | (R)-1-(4-trifluoromethoxy)biphenyl-2-ylcarbamoyl)pyrrolidine-2-carboxylic acid<br><br>ESN [M − H]⁻: 393.3 | A, B | R-proline (CAS# 344-25-2); 4-(trifluoromethoxy)biphenyl-2-amine (Intermediate I17) |
| 18 | (R)-1-(4,6-dichlorobiphenyl-2-ylcarbamoyl)pyrrolidine-2-carboxylic acid<br><br>ESN [M − H]⁻: 377.3 | A, B | R-proline (CAS# 344-25-2); 4,6-dichlorobiphenyl-2-amine (CAS# 783251-09-2) |
| 19 | (R)-1-(5′-chloro-[1,1′;2′,1″]terphenyl-3′-ylcarbamoyl)-pyrrolidine-2-carboxylic acid<br><br>ESN [M − H]⁻: 419.0 | A, B | R-proline (CAS# 344-25-2); 5′-Chloro-[1,1′;2′,1″]terphenyl-3′-ylamine (Intermediate I19) |

-continued

| Example | Name / Structure / MS | Method | Reagents |
|---|---|---|---|
| 20 | (R)-1-(4-cyanobiphenyl-2-ylcarbamoyl)pyrrolidine-2-carboxylic acid<br><br>ESP [M + H]+: 336.1 | A, B | R-proline (CAS# 344-25-2); 2-aminobiphenyl-4-carbonitrile (CAS# 166263-25-8) |
| 21 | (R)-1-(2-phenylbenzo[b]thiophen-3-ylcarbamoyl)pyrrolidine-2-carboxylic acid<br><br>ESN [M − H]−: 365.3 | A, B | R-proline (CAS# 344-25-2); 2-phenylbenzo[b]thiophen-3-amine (CAS# 67447-50-1) |
| 22 | (R)-1-(2-phenylthieno[2,3-b]pyridin-3-ylcarbamoyl)pyrrolidine-2-carboxylic acid<br><br>ESN [M − H]−: 366.0 | A, B | R-proline (CAS# 344-25-2); 2-phenylthieno[2,3-b]pyridin-3-amine |
| 23 | (R)-1-(6-allyl-4-chlorobiphenyl-2-ylcarbamoyl)pyrrolidine-2-carboxylic acid<br><br>ESN [M − H]−: 382.9 | A, B | R-proline (CAS# 344-25-2); 6-allyl-4-chlorobiphenyl-2-amine (Intermediate I23) |

-continued

| Example | Name / Structure / MS | Method | Reagents |
|---|---|---|---|
| 24 | (R)-1-(2-phenylthiophen-3-ylcarbamoyl)pyrrolidine-2-carboxylic acid 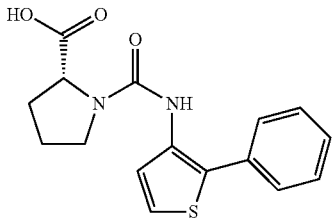 ESN [M + H]+: 314.9 | A, B | R-proline (CAS# 344-25-2); 2-phenylthiophen-3-amine (CAS# 183676-85-9) |
| 25 | (R)-1-(4-chloro-6-cyanobiphenyl-2-ylcarbamoyl)pyrrolidine-2-carboxylic acid 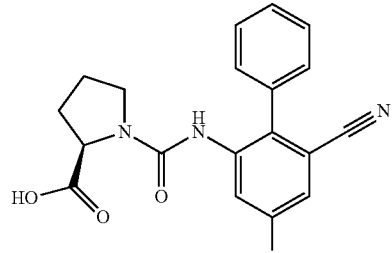 ESN [M − H]−: 368.0 | A, B | R-proline (CAS# 344-25-2); 6-amino-4-chlorobiphenyl-2-carbonitrile (Intermediate I25) |
| 26 | (R)-1-[4-chloro-6-(cyclohexen-1-yl)-biphenyl-2-ylcarbamoyl]pyrrolidine-2-carboxylic acid 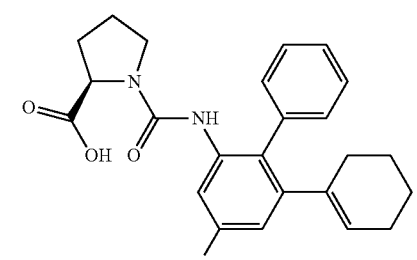 ESN [M − H]−: 423.1 | A, B | R-proline (CAS# 344-25-2); 4-chloro-6-(cyclohexen-1-yl)-biphenyl-2-amine (Intermediate I26) |
| 27 | (S)-1-(4-chlorobiphenyl-2-ylcarbamoyl)azetidine-2-carboxylic acid 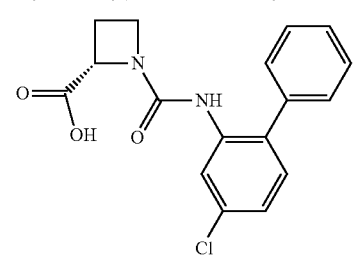 ESN [M − H]−: 329.6 | A, B | (S)-azetidine-2-carboxylic acid (CAS# 2133-34-8); 2-amino-4-chlorobiphenyl (CAS# 90-48-2) |

-continued

| Example | Name / Structure / MS | Method | Reagents |
|---|---|---|---|
| 28 | (R)-1-(biphenyl-2-ylcarbamoyl)azetidine-2-carboxylic acid<br><br>ESN [M − H]⁻: 295.6 | B | (R)-azetidine-2-carboxylic acid (CAS# 7729-30-8); 2-biphenylisocyanate (CAS# 17337-13-2) |
| 29 | (R)-1-(4-chloro-4'-fluorobiphenyl-2-ylcarbamoyl)azetidine-2-carboxylic acid<br><br>ESN [M − H]⁻: 347.6 | A, B | (R)-azetidine-2-carboxylic acid (CAS# 7729-30-8); 4-chloro-4'-fluorobiphenyl-2-amine (Intermediate I29) |
| 30 | (R)-1-(4-chloro-5-fluorobiphenyl-2-ylcarbamoyl)azetidine-2-carboxylic acid<br><br>ESN [M − H]⁻: 347.6 | A, B | (R)-azetidine-2-carboxylic acid (CAS# 7729-30-8); 4-chloro-5-fluorobiphenyl-2-amine (Intermediate I30) |
| 31 | (R)-1-(4-chloro-5-methylbiphenyl-2-ylcarbamoyl)azetidine-2-carboxylic acid<br><br>ESN [M − H]⁻: 343.6 | A, B | (R)-azetidine-2-carboxylic acid (CAS# 7729-30-8); 4-chloro-5-methylbiphenyl-2-amine (Intermediate I31) |

| Example | Name / Structure / MS | Method | Reagents |
|---|---|---|---|
| 36 | (R)-1-(4-chloro-2',3'-difluorobiphenyl-2-ylcarbamoyl)azetidine-2-carboxylic acid<br><br>ESP [M + H]$^+$: 367.4 | C | (R)-azetidine-2-carboxylic acid (CAS# 7729-30-8); 4-chloro-2',3'-difluorobiphenyl-2-amine (Intermediate I36) |
| 37 | (R)-1-(4-chloro-2'-fluorobiphenyl-2-ylcarbamoyl)azetidine-2-carboxylic acid<br><br>ESP [M + H]$^+$: 349.4 | C | (R)-azetidine-2-carboxylic acid (CAS# 7729-30-8); 4-chloro-2'-fluorobiphenyl-2-amine (Intermediate I37) |
| 38 | (R)-1-(4-chloro-3'-fluorobiphenyl-2-ylcarbamoyl)azetidine-2-carboxylic acid<br><br>ESP [M + H]$^+$: 349.4 | C | (R)-azetidine-2-carboxylic acid (CAS# 7729-30-8); 4-chloro-3'-fluorobiphenyl-2-amine (Intermediate I38) |
| 39 | (R)-1-(4-chloro-3',5'-difluorobiphenyl-2-ylcarbamoyl)azetidine-2-carboxylic acid<br><br>ESP [M + H]$^+$: 367.4 | C | (R)-azetidine-2-carboxylic acid (CAS# 7729-30-8); 4-chloro-3',5'-difluorobiphenyl-2-amine (Intermediate I39) |

-continued

| Example | Name / Structure / MS | Method | Reagents |
|---|---|---|---|
| 52 | (R)-1-(5-chloro-2-(thiophen-3-yl)phenyl-carbamoyl)pyrrolidine-2-carboxylic acid<br><br>ESN [M − H]⁻: 348.9 | D | (R)-1-(2-bromo-5-chloro-phenylcarbamoyl)pyrrolidine-2-carboxylic acid (Intermediate I52); thiophen-3-ylboronic acid (CAS# 6165-69-1) |
| 53 | (R)-1-(2-(benzo[b]thiophen-3-yl)-5-chlorophenylcarbamoyl)pyrrolidine-2-carboxylic acid<br><br>ESN [M − H]⁻: 398.9 | D | (R)-1-(2-bromo-5-chloro-phenylcarbamoyl)pyrrolidine-2-carboxylic acid (Intermediate I52); benzo[b]thiophen-3-ylboronic acid (CAS# 113893-08-6) |
| 54 | (R)-1-(4-chloro-4'-fluorobiphenyl-2-ylcarbamoyl)pyrrolidine-2-carboxylic acid<br><br>ESP [M + H]⁺: 363.09 | D | (R)-1-(2-bromo-5-chloro-phenylcarbamoyl)pyrrolidine-2-carboxylic acid (Intermediate I52); 4-fluorophenylboronic acid (CAS# 1765-93-1) |
| 55 | (R)-1-(3',4-dichlorobiphenyl-2-ylcarbamoyl)pyrrolidine-2-carboxylic acid<br><br>ESN [M − H]⁻: 377.1 | D | (R)-1-(2-bromo-5-chloro-phenylcarbamoyl)pyrrolidine-2-carboxylic acid (Intermediate I52); 3-chlorophenylboronic acid (CAS# 63503-60-6) |

| Example | Name / Structure / MS | Method | Reagents |
|---|---|---|---|
| 56 | (R)-1-(3'-carbamoyl-4-chlorobiphenyl-2-ylcarbamoyl)pyrrolidine-2-carboxylic acid<br><br>ESN [M − H]⁻: 385.9 | D | (R)-1-(2-bromo-5-chloro-phenylcarbamoyl(pyrrolidine-2-carboxylic acid (Intermediate I52); 3-carbamoylphenylboronic acid (CAS# 351422-73-6) |
| 57 | (R)-1-[5-chloro-2-(cyclohexen-1-yl)phenyl-carbamoyl]pyrrolidine-2-carboxylic acid<br><br>ESP [M + H]⁺: 349.1316 | D | (R)-1-(2-bromo-5-chloro-phenylcarbamoyl)pyrrolidine-2-carboxylic acid (Intermediate I52); 2-(1-cyclohexen-1-yl)-4,4,5,5-tetramethyl-1,3,2-dioxaborolane (CAS# 141091-37-4) |
| 58 | (R)-1-(5-chloro-2-(pyridin-4-yl)phenylcarbamoyl)pyrrolidine-2-carboxylic acid<br><br>ESN [M − H]⁻: 344.0 | D | (R)-1-(2-bromo-5-chloro-phenylcarbamoyl(pyrrolidine-2-carboxylic acid (Intermediate I52); pyridin-4-ylboronic acid (CAS# 1692-15-5) |
| 59 | (R)-1-(4,4'-dichlorobiphenyl-2-ylcarbamoyl)pyrrolidine-2-carboxylic acid<br><br>ESP [M + H]⁺: 379.1 | D | (R)-1-(2-bromo-5-chloro-phenylcarbamoyl(pyrrolidine-2-carboxylic acid (Intermediate I52); 4-chlorophenylboronic acid (CAS# 1679-18-1) |

| Example | Name / Structure / MS | Method | Reagents |
|---|---|---|---|
| 60 | (R)-1-(4-chloro-4'-methoxybiphenyl-2-ylcarbamoyl)pyrrolidine-2-carboxylic acid<br><br>ESP [M + H]⁺: 375.0 | D | (R)-1-(2-bromo-5-chloro-phenylcarbamoyl)pyrrolidine-2-carboxylic acid (Intermediate I52); 4-methoxyphenylboronic acid (CAS# 5720-07-0) |
| 61 | (R)-1-(4-chloro-2'-methylbiphenyl-2-ylcarbamoyl)pyrrolidine-2-carboxylic acid<br><br>ESP [M + H]⁺: 359.0 | D | (R)-1-(2-bromo-5-chloro-phenylcarbamoyl(pyrrolidine-2-carboxylic acid (Intermediate I52); o-tolylboronic acid (CAS# 16419-60-6) |
| 62 | (R)-1-(4-ethylbiphenyl-2-ylcarbamoyl)pyrrolidine-2-carboxylic acid<br><br>ESN [M − H]⁻: 337.3 | D | (R)-1-(2-bromo-5-ethyl-phenylcarbamoyl)pyrrolidine-2-carboxylic acid (Intermediate I62); phenylboronic acid (CAS# 98-80-6) |
| 63 | (R)-1-(4-chloro-2',4'-difluorobiphenyl-2-ylcarbamoyl)azetidine-2-carboxylic acid<br><br>ESP [M + H]⁺: 367.4 | C | (R)-azetidine-2-carboxylic acid (CAS# 7729-30-8); 4-chloro-2',4'-difluorobiphenyl-2-amine (CAS# 1501401-97-3) |

-continued

| Example | Name / Structure / MS | Method | Reagents |
|---|---|---|---|
| 64 | (R)-1-(4-chloro-4'-fluoro-6-methoxy-biphenyl-2-ylcarbamoyl)azetidine-2-carboxylic acid<br>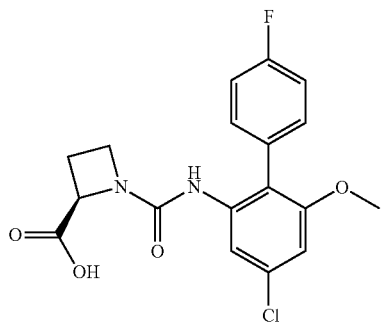<br>ESP [M + H]+: 379.4 | C | (R)-azetidine-2-carboxylic acid (CAS# 7729-30-8); 4-chloro-4'-fluoro-6-methoxybiphenyl-2-amine (Intermediate I64) |

Synthesis of Intermediates

Intermediate I14

4,6-Difluorobiphenyl-2-amine

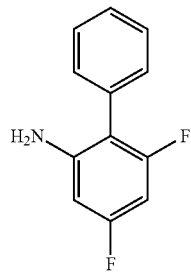

Step 1:

A solution of 2,4-difluoro-6-nitroaniline (CAS#364-30-7; 2.00 g) in DCM (97 ml) was cooled to 0° C. At this temperature boron trifluoride ethyletherate (1.61 g) was added, followed by tert-butyl nitrite (1.63 g). The resulting reaction mixture was allowed to warm to r.t. and stirred for 1 h. The liquid was poured out of the flask and the oily residue was washed with DCM, then the residue was dried under high vacuum and used without further purification for the next step.

Step 2:

The product of step 1 (2.18 g) and phenylboronic acid (1.0 g) were combined with 1,4-dioxane (20 ml), then palladium (II) acetate (55.2 mg) was added to give a foaming dark brown solution. The reaction mixture was stirred at r.t. overnight and then concentrated in vacuo. The product was purified by flash chromatography (silica gel, 0% to 50% EtOAc in heptane) to give 2,4-difluoro-6-nitrobiphenyl (688 mg) as a brown oil.

Step 3:

2,4-Difluoro-6-nitrobiphenyl (684 mg) and sodium sulfite nonahydrate (2.08 g) were combined with ethanol (3.56 ml) and water (3.56 ml) to give a brown solution. The reaction mixture was stirred for 4.5 h at 100° C. and overnight at r.t. The reaction mixture was concentrated in vacuo. The residue was dissolved in EtOAc. The organic layer was washed with water, the aqueous layers were extracted with EtOAc. The combined organic layers were dried over MgSO4, filtered and concentrated in vacuo. The product was purified by flash chromatography (silica gel, 0% to 50% EtOAc in heptane) to give the title compound (469 mg) as a light yellow liquid.

Intermediate I17

4-(Trifluoromethoxy)biphenyl-2-amine

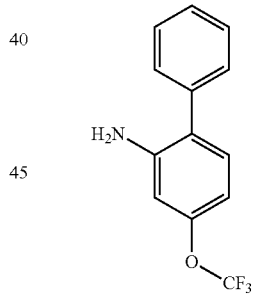

2-Bromo-5-(trifluoromethoxy)aniline (CAS#887267-47-2; 200 mg), phenylboronic acid (143 mg) and a 2 M aqueous solution of sodium carbonate (1.17 ml) were combined at r.t. under argon with dioxane (9.4 ml) and water (3.75 ml). [1,1'-Bis(diphenylphosphino)ferrocene]dichloropalladium (II), dichloromethane adduct (31.9 mg) was added to give yellow suspension. The reaction mixture was heated to 80° C. and stirred overnight at 80° C. The reaction mixture was cooled down and filtered through glass fiber paper, washed with 30 mL water and 30 mL EtOAc, the layers were separated, the aqueous layer was back-extracted with EtOAc. The organic layers were combined, dried over MgSO4 and concentrated in vacuo. The product was purified by flash chromatography (silical gel, 0% to 70% EtOAc in n-heptane) to give the title compound (198 mg) as a yellow oil.

Intermediate I19

5'-Chloro-[1,1';2',1"] terphenyl-3'-ylamine

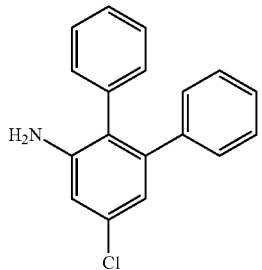 [SMILES: Nc1cc(Cl)cc(-c2ccccc2)c1-c1ccccc1]

Step 1:

To a solution of 2,4-dichloro-6-nitrophenol (CAS#609-89-2; 2.4 g) in DCM (150 ml) was added triethylamine (2.69 g). The reaction mixture was cooled to −20° C., trifluoromethanesulfonic anhydride (3.91 g) was added slowly at this temperature and stirred for 20 min. The cooling-bath was removed and the reaction mixture was stirred for 1 h at r.t. The reaction mixture was washed with a saturated aqueous $NH_4Cl$ solution and brine, the aqueous layers were extracted with DCM. The combined organic layers were dried over $MgSO_4$, filtered and concentrated in vacuo. The product was purified by flash chromatography (silica gel, 50 g, 0% to 40% EtOAc in heptane) to give 2,4-dichloro-6-nitrophenyl trifluoromethanesulfonate (3.9 g) as a light yellow solid.

Step 2:

2,4-Dichloro-6-nitrophenyl trifluoromethanesulfonate (3.94 g), phenylboronic acid (2.12 g) and 1,1'-bis(diphenylphosphino)ferrocene-palladium(II)dichloride, dichloromethane complex (474 mg) were combined with dioxane (34.1 ml), a 2 M aqueous sodium carbonate solution (17.4 ml) and water (24.7 ml) to give an orange suspension. The reaction mixture was stirred at 80° C. for 3.5 h. The reaction mixture was cooled down, then filtered through glass fiber paper and washed with EtOAc and $KHSO_4$-solution. The filtrate was extracted with EtOAc, the organic layers were washed with brine, dried over $MgSO_4$ and concentrated in vacuo. The product was purified by flash chromatography (silica gel, 70 g, 0% to 50% EtOAc in n-hexane) followed by preparative HPLC to give 5'-chloro-3'-nitro-[1,1';2',1"] terphenyl (455 mg) as an off-white solid.

Step 3:

5'-Chloro-3'-nitro-[1,1';2',1"]terphenyl (437 mg), iron powder (473 mg) and ammonium chloride (75.5 mg) were combined with ethanol (7.15 ml) and water (0.64 ml) to give a white suspension. The reaction mixture was heated to 85° C. (reflux) and stirred for 6.5 h, then at r.t. over night. Iron powder (145 mg) and ammonium chloride (25 mg) were added and the reaction was heated again to 85° C. for 2.5 h, then again over night at r.t. The reaction mixture was filtered through glass filter paper and concentrated in vacuo. The raw product was extracted with EtOAc, the organic phases were washed with $NaHCO_3$ solution and brine. The organic layers were dried over $MgSO_4$, filtered and concentrated in vacuo. The product was purified by flash chromatography (silica gel, 0% to 20% EtOAc in heptane) to give the title compound (356 mg) as an off-white solid.

Intermediate I23

6-Allyl-4-chlorobiphenyl-2-amine

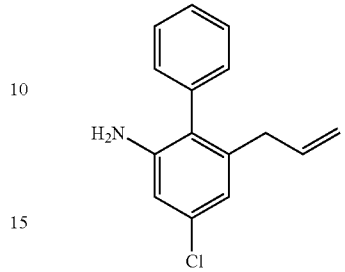

Step 1:

In analogy to the synthesis of Intermediate I19, step 1, 2-allyl-4-chloro-6-nitrophenol (CAS#569688-58-0) was converted to 2-allyl-4-chloro-6-nitrophenyl trifluoromethanesulfonate.

Step 2:

In analogy to the synthesis of Intermediate I19, step 2, 2-allyl-4-chloro-6-nitrophenyl trifluoromethanesulfonate was reacted with phenylboronic acid to give 2-allyl-4-chloro-6-nitrobiphenyl.

Step 3:

In analogy to the synthesis of Intermediate I19, step 3, 2-allyl-4-chloro-6-nitrobiphenyl was reduced with iron to give the title compound as a light yellow liquid.

Intermediate I25

6-Amino-4-chlorobiphenyl-2-carbonitrile

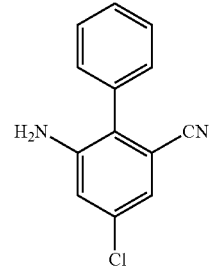 [SMILES: N#Cc1cc(Cl)cc(N)c1-c1ccccc1]

Step 1:

In analogy to the synthesis of Intermediate I19, step 1, 5-chloro-2-hydroxy-3-nitrobenzonitrile (CAS#88310-62-7) was converted to 4-chloro-2-cyano-6-nitrophenyl trifluoromethanesulfonate.

Step 2:

In analogy to the synthesis of Intermediate I19, step 2, 4-chloro-2-cyano-6-nitrophenyl trifluoromethanesulfonate was reacted with phenylboronic acid to give 4-chloro-6-nitrobiphenyl-2-carbonitrile.

Step 3:

In analogy to the synthesis of Intermediate I19, step 3, 4-chloro-6-nitrobiphenyl-2-carbonitrile was reduced with iron to give the title compound as a light yellow solid.

Intermediate I26

4-Chloro-6-(cyclohexen-1-yl)-biphenyl-2-amine

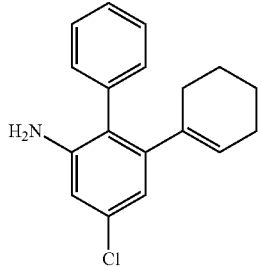 [SMILES: Nc1cc(Cl)cc(C2=CCCCC2)c1-c1ccccc1]

Step 1:
In analogy to the synthesis of Intermediate I19, step 2, 2-bromo-4-chloro-6-nitrophenol (CAS#15969-10-5) was reacted with cyclohexenylboronic acid to give 4-chloro-2-cyclohexenyl-6-nitrophenol.

Step 2:
In analogy to the synthesis of Intermediate I19, step 1, 4-chloro-2-cyclohexenyl-6-nitrophenol was converted to 4-chloro-2-cyclohexenyl-6-nitrophenyl trifluoromethanesulfonate.

Step 3:
In analogy to the synthesis of Intermediate I19, step 2, 4-chloro-2-cyclohexenyl-6-nitrophenyl trifluoromethanesulfonate was reacted with phenylboronic acid to give 4-chloro-2-cyclohexenyl-6-nitrobiphenyl.

Step 4:
In analogy to the synthesis of Intermediate I19, step 3, 4-chloro-2-cyclohexenyl-6-nitrobiphenyl was reduced with iron to give the title compound as brown oil.

Intermediate I29

4-Chloro-4'-fluorobiphenyl-2-amine

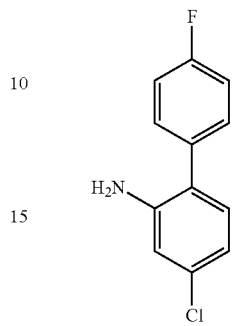

2-Bromo-5-chloroaniline (CAS#823-57-4; 5 g), 4-fluorophenylboronic acid (3.56 g) and cesium carbonate (31.6 g) were combined in THF (70 ml) and water (35 ml). The mixture was degassed by bubbling argon through the solution. After addition of [1,1'-bis(diphenylphosphino)ferrocene]dichloropalladium(II) (886 mg) the reaction mixture was stirred 1 h at 80° C. in a sealed tube. The reaction mixture was diluted with EtOAc, washed with water, dried over $Na_2SO_4$, evaporated and purified by chromatography (silica gel, 0% to 30% EtOAc in heptane). The product was finally bulb-to-bulb distilled at 0.3 mbar and 120-130° C. oven temperature to give the title compound (5.07 g) as a light yellow liquid.

In analogy to the synthesis of Intermediate I29, the following intermediates were prepared:

| Intermediate | Name | Structure | Reagents |
|---|---|---|---|
| I30 | 4-chloro-5-fluorobiphenyl-2-amine | 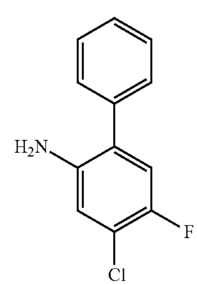 [SMILES: Nc1cc(Cl)c(F)cc1-c1ccccc1] | 2-bromo-5-chloro-4-fluoroaniline (CAS# 85462-59-5); phenylboronic acid |
| I31 | 4-chloro-5-methylbiphenyl-2-amine | 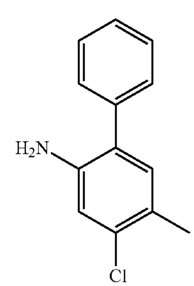 | 2-bromo-5-chloro-4-methylaniline (CAS# 102170-52-5); phenylboronic acid |

-continued

| Intermediate | Name | Structure | Reagents |
|---|---|---|---|
| I36 | 4-chloro-2',3'-difluorobiphenyl-2-amine | 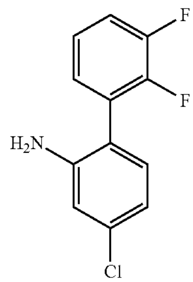 [SMILES: Nc1cc(Cl)ccc1-c1cccc(F)c1F] | 2-bromo-5-chloroaniline (CAS# 823-57-4); 2,3-difluorophenylboronic acid |
| I37 | 4-chloro-2'-fluorobiphenyl-2-amine | 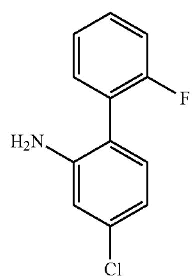 [SMILES: Nc1cc(Cl)ccc1-c1ccccc1F] | 2-bromo-5-chloroaniline (CAS# 823-57-4); 2-fluorophenylboronic acid |
| I38 | 4-chloro-3'-fluorobiphenyl-2-amine | 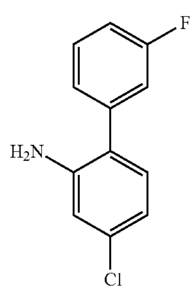 [SMILES: Nc1cc(Cl)ccc1-c1cccc(F)c1] | 2-bromo-5-chloroaniline (CAS# 823-57-4); 3-fluorophenylboronic acid |
| I39 | 4-chloro-3',5'-difluorobiphenyl-2-amine | 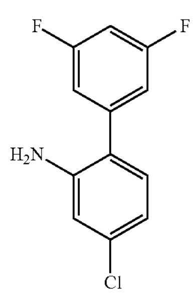 [SMILES: Nc1cc(Cl)ccc1-c1cc(F)cc(F)c1] | 2-bromo-5-chloroaniline (CAS# 823-57-4); 3,5-difluorophenylboronic acid |

Intermediate I52

(R)-1-(2-bromo-5-chlorophenylcarbamoyl)pyrrolidine-2-carboxylic acid

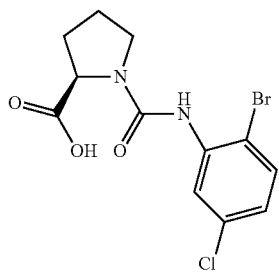 [SMILES: O=C(O)[C@H]1CCCN1C(=O)Nc1cc(Cl)ccc1Br]

R-Proline (CAS#344-25-2) was reacted with 1-bromo-4-chloro-2-isocyanatobenzene (CAS#1261815-71-7) according to General Method B to give the title compound as an off-white solid.

Intermediate I62

(R)-1-(2-bromo-5-ethylphenylcarbamoyl)pyrrolidine-2-carboxylic acid

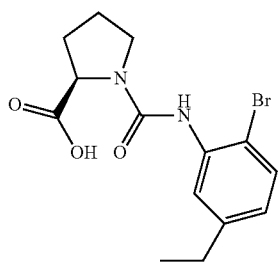 [SMILES: CCc1ccc(Br)c(NC(=O)N2CCC[C@@H]2C(=O)O)c1]

R-Proline (CAS#344-25-2) was reacted with 2-bromo-5-ethylaniline (CAS#80948-73-8) according to General Methods A and B to give the title compound as an off-white solid.

Intermediate I64

4-Chloro-4'-fluoro-6-methoxybiphenyl-2-amine

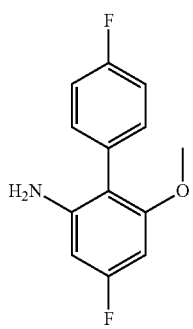 [SMILES: COc1cc(F)cc(N)c1-c1ccc(F)cc1]

Step 1:

To a solution of 4-chloro-2-methoxy-6-nitrophenol (CAS#118724-89-3; 3.78 g) in DCM (200 ml) under argon was added triethylamine (4.32 g). The reaction mixture was cooled to −20° C., then trifluoromethanesulfonic anhydride (6.41 g) was added dropwise. The mixture was stirred for 20 min, then the cooling bath was removed and the reaction mixture was stirred at r.t. for 2.5 h. The crude reaction mixture was washed with sat. aqueous $NH_4Cl$ solution and with brine. The aqeuos layers were extracted with DCM. The combined organic layers were dried over $MgSO_4$, filtered and concentrated in vacuo. The crude material was purified by flash chromatography (silica gel, 0% to 100% EtOAc in n-heptane) to give 4-chloro-2-methoxy-6-nitrophenyl trifluoromethanesulfonate (6.23 g) as a yellow solid.

Step 2:

In analogy to the synthesis of Intermediate I19, step 2, 4-chloro-2-methoxy-6-nitrophenyl trifluoromethanesulfonate was reacted with 4-fluorophenylboronic acid to give 4-chloro-4'-fluoro-2-methoxy-6-nitrobiphenyl as a yellow solid.

Step 3:

In analogy to the synthesis of Intermediate I19, step 3, 4-chloro-4'-fluoro-2-methoxy-6-nitrobiphenyl was reduced with iron to give the title compound as a yellow oil which was used as a crude product for the next step.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. The compound selected from the group consisting of:
1-(Biphenyl-2-ylcarbamoyl)-piperidine-2-carboxylic acid;
(R)-1-(5-chlorobiphenyl-2-ylcarbamoyl)pyrrolidine-2-carboxylic acid;
(R)-1-(2-phenoxyphenylcarbamoyl)pyrrolidine-2-carboxylic acid;
(R)-1-(2-benzylphenylcarbamoyl)pyrrolidine-2-carboxylic acid;

(R)-1-(5-chloro-2-phenoxyphenylcarbamoyl)pyrrolidine-2-carboxylic acid;
1-(Biphenyl-2-ylcarbamoyl)-2-phenyl-pyrrolidine-2-carboxylic acid;
3-(Biphenyl-2-ylcarbamoyl)-thiazolidine-2-carboxylic acid;
(S)-3-(Biphenyl-2-ylcarbamoyl)-thiazolidine-4-carboxylic acid;
(1SR,2SR,5RS)-3-(Biphenyl-2-ylcarbamoyl)-3-aza-bicyclo[3.1.0]hexane-2-carboxylic acid;
(R)-1-(4-chlorobiphenyl-2-ylcarbamoyl)pyrrolidine-2-carboxylic acid;
(R)-1-(3-fluorobiphenyl-2-ylcarbamoyl)pyrrolidine-2-carboxylic acid;
(R)-1-(4-chlorobiphenyl-2-ylcarbamoyl)azetidine-2-carboxylic acid;
(R)-1-(4-(trifluoromethyl)biphenyl-2-ylcarbamoyl)pyrrolidine-2-carboxylic acid;
(R)-1-(4,6-difluorobiphenyl-2-ylcarbamoyl)pyrrolidine-2-carboxylic acid;
1-(biphenyl-2-ylcarbamoyl)-2-methylpyrrolidine-2-carboxylic acid;
(R)-1-(4-fluorobiphenyl-2-ylcarbamoyl)pyrrolidine-2-carboxylic acid;
(R)-1-(4-(trifluoromethoxy)biphenyl-2-ylcarbamoyl)pyrrolidine-2-carboxylic acid;
(R)-1-(4,6-dichlorobiphenyl-2-ylcarbamoyl)pyrrolidine-2-carboxylic acid;
(R)-1-(5'-Chloro-[1,1';2',1"]terphenyl-3'-ylcarbamoyl)-pyrrolidine-2-carboxylic acid;
(R)-1-(4-cyanobiphenyl-2-ylcarbamoyl)pyrrolidine-2-carboxylic acid;
(R)-1-(2-phenylbenzo[b]thiophen-3-ylcarbamoyl)pyrrolidine-2-carboxylic acid;
(R)-1-(2-phenylthieno[2,3-b]pyridin-3-ylcarbamoyl)pyrrolidine-2-carboxylic acid;
(R)-1-(6-allyl-4-chlorobiphenyl-2-ylcarbamoyl)pyrrolidine-2-carboxylic acid;
(R)-1-(2-phenylthiophen-3-ylcarbamoyl)pyrrolidine-2-carboxylic acid;
(R)-1-(4-chloro-6-cyanobiphenyl-2-ylcarbamoyl)pyrrolidine-2-carboxylic acid;
(R)-1-[4-chloro-6-(cyclohexen-1-yl)-biphenyl-2-ylcarbamoyl]pyrrolidine-2-carboxylic acid;
(S)-1-(4-chlorobiphenyl-2-ylcarbamoyl)azetidine-2-carboxylic acid;
(R)-1-(biphenyl-2-ylcarbamoyl)azetidine-2-carboxylic acid;
(R)-1-(4-chloro-4'-fluorobiphenyl-2-ylcarbamoyl)azetidine-2-carboxylic acid;
(R)-1-(4-chloro-5-fluorobiphenyl-2-ylcarbamoyl)azetidine-2-carboxylic acid;
(R)-1-(4-chloro-5-methylbiphenyl-2-ylcarbamoyl)azetidine-2-carboxylic acid;
(R)-1-(4-chloro-2',3'-difluorobiphenyl-2-ylcarbamoyl)azetidine-2-carboxylic acid;
(R)-1-(4-chloro-2'-fluorobiphenyl-2-ylcarbamoyl)azetidine-2-carboxylic acid;
(R)-1-(4-chloro-3'-fluorobiphenyl-2-ylcarbamoyl)azetidine-2-carboxylic acid;
(R)-1-(4-chloro-3',5'-difluorobiphenyl-2-ylcarbamoyl)azetidine-2-carboxylic acid;
(R)-1-(5-chloro-2-(thiophen-3-yl)phenylcarbamoyl)pyrrolidine-2-carboxylic acid;
(R)-1-(2-(benzo[b]thiophen-3-yl)-5-chlorophenylcarbamoyl)pyrrolidine-2-carboxylic acid;
(R)-1-(4-chloro-4'-fluorobiphenyl-2-ylcarbamoyl)pyrrolidine-2-carboxylic acid;
(R)-1-(3',4-dichlorobiphenyl-2-ylcarbamoyl)pyrrolidine-2-carboxylic acid;
(R)-1-(3'-carbamoyl-4-chlorobiphenyl-2-ylcarbamoyl)pyrrolidine-2-carboxylic acid;
(R)-1-[5-chloro-2-(cyclohexen-1-yl)phenylcarbamoyl]pyrrolidine-2-carboxylic acid;
(R)-1-(5-chloro-2-(pyridin-4-yl)phenylcarbamoyl)pyrrolidine-2-carboxylic acid;
(R)-1-(4,4'-dichlorobiphenyl-2-ylcarbamoyl)pyrrolidine-2-carboxylic acid;
(R)-1-(4-chloro-4'-methoxybiphenyl-2-ylcarbamoyl)pyrrolidine-2-carboxylic acid;
(R)-1-(4-chloro-2'-methylbiphenyl-2-ylcarbamoyl)pyrrolidine-2-carboxylic acid;
(R)-1-(4-ethylbiphenyl-2-ylcarbamoyl)pyrrolidine-2-carboxylic acid;
(R)-1-(4-chloro-2',4'-difluorobiphenyl-2-ylcarbamoyl)azetidine-2-carboxylic acid;
(R)-1-(4-chloro-4'-fluoro-6-methoxybiphenyl-2-ylcarbamoyl)azetidine-2-carboxylic acid;
and pharmaceutically acceptable salts thereof.

2. The compound according to claim 1, selected from the group consisting of:
(R)-1-(4-chlorobiphenyl-2-ylcarbamoyl)azetidine-2-carboxylic acid;
(R)-1-(4-chloro-4'-fluorobiphenyl-2-ylcarbamoyl)azetidine-2-carboxylic acid;
and pharmaceutically acceptable salts thereof.

3. A pharmaceutical composition comprising a compound according to claim 1 and a therapeutically diluent, carrier or excipient.

* * * * *